US006083915A

United States Patent [19]
Bogden et al.

[11] Patent Number: 6,083,915
[45] Date of Patent: Jul. 4, 2000

[54] METHOD FOR TREATING LIVER CANCER

[75] Inventors: Arthur E. Bogden, Hopedale, Mass.; David H. Coy, New Orleans, La.; Sun Hyuk Kim, Chestnut Hill; Jacques-Pierre Moreau, Upton, both of Mass.

[73] Assignees: Biomeasure, Inc., Milford, Mass.; The Administration of the Tulane Educational Fund, New Orleans, La.

[21] Appl. No.: 07/698,681

[22] Filed: May 10, 1991

[51] Int. Cl.$^7$ .................................................. A61K 38/08
[52] U.S. Cl. .............................. 514/15; 514/894; 530/828
[58] Field of Search ........................ 514/15, 894; 530/828

[56] References Cited

U.S. PATENT DOCUMENTS

| 5,068,222 | 11/1991 | Camble et al. | 514/15 |
| 5,081,107 | 1/1992 | Cotton et al. | 514/15 |

FOREIGN PATENT DOCUMENTS

WO 91/04040  4/1991  WIPO.

OTHER PUBLICATIONS

Per O.Seglen, et al., Neuroendocrine dysdifferentiation and bombesin production in carcinogen–induced hepatocellular rat tumours, Carcinogenesis, vol. 10, No. 1, pp. 21–25, 1989.

J of Biol Chem., vol. 262, No. 34, pp. 16456–16460, 1987, Heikkila et al.

Cancer Research, Alexander et al., Effects of Bombesin on Growth of Human Small Cell Lung Carcinoma In Vivo., vol. 48, pp. 1439–1441 (1988).

S. M. Kaftan et al., "Bombesin and Hepatocyte Proliferation", Chemical Carcinogenesis 2 Modulating Factors pp. 619–623, 1989.

*Primary Examiner*—F. T. Moezie
*Assistant Examiner*—Dinc Plunkett
*Attorney, Agent, or Firm*—Fish & Richardson, P.C.; William F. McGowan

[57] ABSTRACT

A method of treating liver cancer involving administration to the subject a therapeutically effective amount of a bombesin analog.

15 Claims, 3 Drawing Sheets

METHOD FOR TREATING LIVER CANCER

BACKGROUND OF THE INVENTION

This invention relates to the treatment of hepatoma, i.e., liver cancer.

The amphibian peptide bombesin, pGlu-Gln-Arg-Leu-Gly-Asn-Gln-Trp-Ala-Val-Gly-His-Leu-Met-NH$_2$ [Anastasi et al., Experientia 27:166–167 (1971)], is closely related to the mammalian gastrin-releasing peptides (GRP), e.g., the porcine GRP, Ala-Pro-Val-Ser-Val-Gly-Gly-Gly-Thr-Val-Leu-Ala-Lys-Met-Tyr-Pro-Arg-Gly-Asn-His-Trp-Ala-Val-Gly-His-Leu-Met-NH$_2$ [McDonald et al., Biochem. Biophys. Res. Commun. 90:227–233 (1979)] and human GRP, Val-Pro-Leu-Pro-Ala-Gly-Gly-Gly-Thr-Val-Leu-Thr-Lys-Met-Tyr-Pro-Arg-Gly-Asn-His-Trp-Ala-Val-Gly-His-Leu-Met-NH$_2$.

Bombesin has been found to be a growth factor for a number of human cancer cell lines, including small-cell lung carcinoma (SCLC), and has been detected in human breast and prostate cancer [Haveman et al., eds. *Recent Results in Cancer Research-Peptide Hormones in Lung Cancer*, Springer-Verlag, New York (1986)]. A number of these cancers are known to secrete peptide hormones related to GRP or bombesin. Consequently, antagonists to bombesin have been proposed as agents for the treatment of these cancers.

Cuttitta et al. demonstrated that a specific monoclonal antibody to bombesin inhibited in vivo the growth of a human small-cell lung cancer cell line xenografted to nude mice (Cuttitta et al., Cancer Survey 4:707–727 (1985)). In 3T3 murine fibroblasts which are responsive to the mitotic effect of bombesin, Zachary and Rozengurt observed that a substance P antagonist (Spantide) acted as a bombesin antagonist [Zachary et al., Proc. Natl. Acad. Sci. (USA), 8:7616–7620 (1985)]. Heinz-Erian et al. replaced His at position 12 in bombesin with D-Phe and observed bombesin antagonist activity in dispersed acini from guinea pig pancreas [Heinz-Erian et al., Am. J. of Physiol. 252:G439–G442 (1987)]. Rivier reported work directed toward restricting the conformational freedom of the bioactive C-terminal decapeptide of bombesin by incorporating intramolecular disulfide bridges; however, Rivier mentioned that bombesin analogs with this modification failed to exhibit any antagonist activity [Rivier et al., *Competitive Antagonists of Peptide Hormones*, in Abstracts of the International Symposium on Bombesin-Like Peptides in Health and Disease, Rome, Italy (October, 1987)].

Bombesin exhibits both direct and indirect effects on the gastrointestinal tract, including the release of hormones and the stimulation of pancreatic, gastric, and intestinal secretion and of intestinal mobility. Gastrin and cholecystokinin (CCK) which are released by bombesin, have been shown to play a role in the maintenance of normal gastrointestinal mucosa as well as in augmenting growth of normal and neoplastic tissues. The growth of xenografted human colon and stomach carcinomas in nude mice has been stimulated by the administration of gastrin and later inhibited with the addition of secretin [Tanake et al., Tokaku J. Exp. Med. 148:459 (1986)] and the growth of MC-26 murine colon carcinoma, which possesses gastrin receptors is stimulated by pentagastrin [Winsett et al., Surgery 99:302, (1980)] and inhibited by proglumide, a gastrin-receptor antagonist [Beauchamp et al., Ann. Surg. 202:303 (1985)]. Bombesin has been found to act concurrently as both a trophic agent for normal host pancreas and a growth inhibitory agent in xenografted human pancreatic tumor tissue [Alexander et al., Pancreas 3:247 (1988)].

Uncommon Abbreviations cyclohexyl-Ala=CHxAla= cyclohexyl alanine

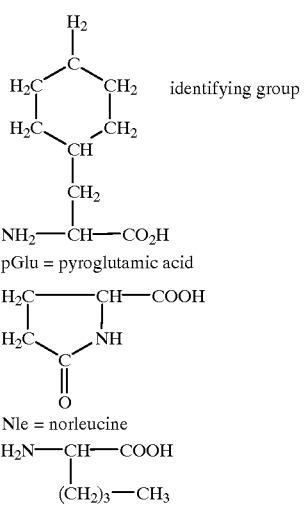

pGlu = pyroglutamic acid

Nle = norleucine

Cpa=para-chloro-phenylalanine

HyPro=hydroxyproline

β-Nal=β-naphthylalanine

Sar=sarcosine

F$_5$-Phe=penta-fluoro-phenylalanine

Sta (statine)=(3S, 4S)-4-amino-3-hydroxy-6-methylheptanoic acid, and has the chemical structure

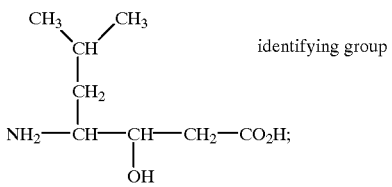

AHPPA=(3S,4S)-4-amino-3-hydroxy-5-phenylpentanoic acid, and has the chemical structure

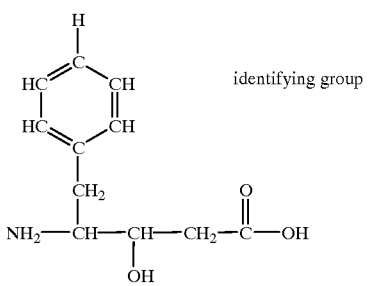

ACHPA=(3S, 4S)-4-amino-5-cyclohexyl-3-hydroxypentanoic acid and has the chemical structure

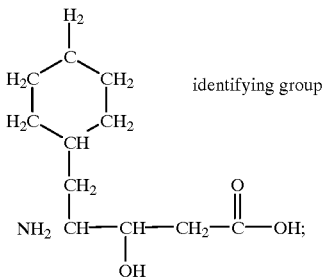

R=right (D) configuration; S=left (L) configuration; and racemate=equal mix of R and S.

1-methyl-His; 3-methyl-His=methyl ($CH_3$) group on nitrogen at positions 1 or 3 of Histidine

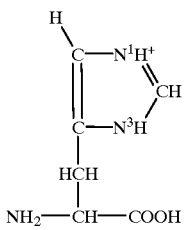

Met-oxide=methionine oxide

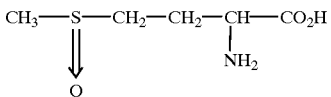

The identifying group of an α-amino acid (for case of pyroglutamate, see below) refers to the atom or group of atoms, other than the α-carbonyl carbon atom, the α-amino nitrogen atom, or the H atom, bound to the asymmetric α-carbon atom. To illustrate by examples, the identifying group of alanine is $CH_3$, the identifying group of valine is $(CH_3)_2CH$, the identifying group of lysine is $H_3N^+(CH_2)_4$ and the identifying group of phenylalanine is $(C_6H_6)CH_2$. The identifying group of a β- or γ-amino acid is the analogous atom or group of atoms bound to the β- or the γ-carbon atom, respectively. Where not specified, the identifying group may be of an α, β, or γ amino acid. In the case of pyroglutamate the identifying group consists of —NH—CO—$CH_2$—$CH_2$—.

SUMMARY OF THE INVENTION

The present invention features a method of treating hepatoma, or liver cancer, in a mammalian subject by administering to the subject a composition containing a therapeutically effective amount of a bombesin analog. The term "bombesin analog" is defined below. One class of bombesin analogs which can be used for the above-described treatment is a peptide containing between seven to ten amino acid residues, inclusive, and having the following generic formula:

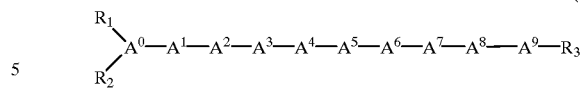

wherein $A^0$=Gly, D- or L-isomer of any of pGlu, Nle, α-aminobutyric acid, Ala, Val, Gln, Asn, Leu, Ile, p-X-Phe (where X=H, F, Cl, Br, $NO_2$, OH, $CH_3$), Trp, β-Nal, Cys, or is deleted;

$A^1$=the D- or L-isomer of any of pGlu, Nle, α-aminobutyric acid, Ala, Val, Gln, Asn, Leu, Ile, p-X-Phe (where X=H, F, Cl, Br, $NO_2$, OH, or $CH_3$), Asp, Glu, $F_5$-Phe, Trp, β-Nal, Cys, Lys, or is deleted;

$A^2$=Gly, D- or L-isomer of any of pGlu, Ala, Val, Gln, Asn, Leu, Ile, p-X-Phe (where X=H, F, Cl, Br, $NO_2$, OH, or $CH_3$), Trp, β-Nal, Asp, Glu, His, 1-methyl-His, 3-methyl-His, Cys, Lys, or is deleted;

$A^3$=the D- or L-isomer of any of p-X-Phe (where X=H, F, Cl, Br, $NO_2$, OH, or $CH_3$), β-Nal, or Trp;

$A^4$=Ala, Val, Gln, Asn, Gly, Leu, Ile, Nle, α-aminobutyric acid, p-X-phe (where X=H, F, Cl, Br, $NO_2$, OH, or $CH_3$), Trp, or β-Nal;

$A^5$=Gln, Asn, Gly, Ala, Leu, Ile, Nle, α-aminobutyric acid, Val, p-X-Phe (where X=H, F, Cl, Br, $NO_2$, OH, or $CH_3$), Trp, Thr, or β-Nal;

$A^6$=Sar, Gly or the D-isomer of any Ala, N-methyl-Ala, Val, Gln, Asn, Leu,-Ile, p-X-Phe (where X=H, F, Cl, Br, $NO_2$, OH, or $CH_3$), Trp, Cys, β-Nal, or is deleted;

$A^7$=1-methyl-His, 3-methyl-His, His, Lys, Asp, or Glu;

$A^8$=Leu, Ile, Val, Nle, α-aminobutyric acid, Trp, Thr, β-Nal, Lys, Asp, Glu, or Cys;

$A^9$=L-isomer of any of Met, Met-oxide, Leu, Ile, Nle, α-aminobutyric acid, p-X-Phe (where X=H, F, Cl, Br, $NO_2$, OH, or $CH_3$), Trp, β-Nal, CHxAla, Cys, or is deleted;

each $R_1$ and $R_2$, independently, is H, $C_{1-12}$ alkyl, $C_{7-10}$ phenylalkyl, $COE_1$ (where $E_1$ is $C_{1-20}$ alkyl, $C_{3-20}$ alkenyl, $C_{3-20}$ alkynyl, phenyl, naphthyl, or $C_{7-10}$ phenylalkyl), or $C_1$–$C_{12}$ acyl, and $R_1$ and $R_2$ are bonded to the nitrogen adjacent to the α-carbon of the N-terminal amino acid residue of the analog; provided that when one of $R_1$ or $R_2$ is $COE_1$ the other must be H; and $R_3$ is OH, $NH_2$, $C_{1-12}$ alkoxy, $C_{7-10}$ phenylalkoxy, or $C_{3-20}$ naphthylalkoxy and is bonded to the α-carbonyl carbon of the C-terminal amino acid residue of the analog;

provided that, if $A^0$ is present, $A^1$ cannot be pGlu; and, if $A^0$ or $A^1$ is present, $A^2$ cannot be pGlu; further provided that, when $A^0$ is deleted and $A^1$ is pGlu, one of $R_1$ and $R_2$ must be H; further provided that, where $A^0$ is deleted and $A^1$ is not pGlu, $A^1$ can be bonded to $A^9$, or where $A^0$ and $A^1$ are deleted and $A^2$ is not pGlu, $A^2$ can be bonded to $A^9$, or where $A^0$, $A^1$, and $A^2$ are deleted, $A^3$ can be bonded to $A^9$; further provided that both terminal residues cannot be Asp or Glu and Lys, respectively, and that side chain carboxyl group of Asp or Glu can be coupled with ε-amino group of Lys through an amide bridge; further provided that either one of $A^1$ or $A^2$ can be Cys and bonded through a disulfide bridge with either $A^8$ or $A^9$, provided that either one of $A^8$ or $A^9$ can be Cys and bonded through a disulfide bridge with either $A^1$ or $A^2$; and further provided that where $A^0$ and $A^1$ are deleted and $A^6$ is D-Ala, $A^8$-$A^9$-$R_3$ cannot be Leu-Met-$NH_2$; or a pharmaceutically acceptable salt thereof.

In this disclosure, for amino acid sequence formulae the N-terminus is at the left and the C-terminus at the right in accordance with the conventional representation of a polypeptide chain. Also, where the amino acid residue is optically active, it is the L-form configuration that is intended unless D-form is expressly designated. Lines between amino acid residues represent peptide bonds which join the amino acids. $COE_1$ stands for

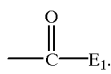

Preferred compounds of generic formula (A) above include those in which:

$A^0$=pGlu, Gly, D-Phe, or is deleted;
$A^1$=pGlu, D-Phe, D-Ala, D-β-Nal, D-Cpa, D-Asn, Cys, or is deleted;
$A^2$=pGlu, Asn, Gln, His, 1-methyl-His, 3-methyl-His, Cys, or is deleted;
$A^3$=Trp;
$A^4$=Ala;
$A^5$=Val;
$A^6$=Sar, Gly, D-Phe, or D-Ala;
$A^7$=His;
$A^8$=Leu, or Cys;
$A^9$=L-isomer of any of Met, Leu, Ile, Nle, Phe, or Cys.

Two particular preferred compounds of generic formula (A) above are:

D-Phe-Gln-Trp-Ala-Val-Gly-His-Leu-Met-$NH_2$ (code named BIM-26218), and

D-Phe-Gln-Trp-Ala-Val-Gly-His-Leu-Leu-$NH_2$ (code named BIM-26187).

Another class bombesin analogs that is suitable in the hepatoma therapy method of the invention includes peptides containing between seven and ten amino acid residues, inclusive, and having the following generic formula:

(B)

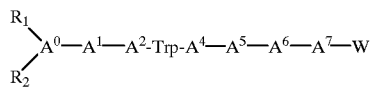

wherein $A^0$=pGlu, Gly, Nle, α-aminobutyric acid, or the D-isomer of any of Ala, Val, Gln, Asn, Leu, Ile, Met, p-X-Phe (where X=F, Cl, Br, $NO_2$, OH, H, or $CH_3$), Trp, Cys, or β-Nal, or is deleted;
$A^1$=the D- or L-isomer of any of pGlu, Nle, α-aminobutyric acid, or the D-isomer of any of Ala, Val, Gln, Asn, Leu, Ile, Met, p-X-Phe (where X=F, Cl, Br, $NO_2$, OH, H, or $CH_3$), $F_5$-Phe, Trp, Cys, or β-Nal, or is deleted;
$A^2$=pGlu, Gly, Ala, Val, Gln, Asn, Leu, Ile, Met, p-X-Phe (where X=F, Cl, Br, $NO_2$, OH, H, or $CH_3$), Trp, Cys, β-Nal, His, 1-methyl-His, or 3-methyl-His;
$A^4$=Ala, Val, Gln, Asn, Gly, Leu, Ile, Nle, α-aminobutyric acid, Met, p-X-Phe (where X=F, Cl, Br, $NO_2$, OH, H, or $CH_3$), Trp, Cys, or β-Nal;
$A^5$=Gln, Asn, Gly, Ala, Leu, Ile, Nle, α-aminobutyric acid, Met, Val, p-X-Phe (where X=F, Cl, Br, OH, H, or $CH_3$), Trp, Thr, or β-Nal;
$A^6$=Sar, Gly, or the D-isomer of any of Ala, N-methyl-Ala, Val, Gln, Asn, Leu, Ile, Net, p-X-Phe (where X=F, Cl, Br, $NO_2$, OH, H, or $CH_3$), Trp, Cys, or β-Nal;
$A^7$=1-methyl-His, 3-methyl-His, or His;

each $R_1$ and $R_2$, independently, is H, $C_{1-12}$ alkyl, $C_{7-10}$ phenylalkyl, $COE_1$ (where $E_1$ is $C_{1-20}$ alkyl, $C_{3-20}$ alkenyl, $C_{3-20}$ alkynyl, phenyl, naphthyl, or $C_{7-10}$ phenylalkyl), or $C_1$–$C_{12}$ acyl, provided that when one of $R_1$ or $R_2$ is $COE_1$, the other must be H; and $R_1$ and $R_2$ are bonded to the nitrogen adjacent to the α-carbon of the N-terminal amino acid residue of the analog;

W is bonded to the α-carbonyl carbon of $A^7$ and is one of the following groups:

(I):

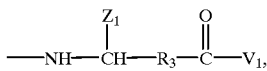

wherein $R_3$ is $CHR_{20}$—$(CH_2)_{n1}$ (where $R_{20}$ is either of H or OH; and n1 is either of 1 or 0), or is deleted, and $Z_1$ is the identifying group of any of the amino acids Gly, Ala, Val, Leu, Ile, Ser, Asp, Asn, Glu, Gln, p-X-Phe (where X=H, F, Cl, Br, $NO_2$, OH, or $CH_3$), $F_5$-Phe, Trp, Cys, Met, Pro, HyPro, cyclohexyl-Ala, or β-Nal; and $V_1$ is either

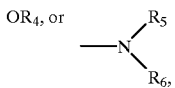

where $R_4$ is any of $C_{1-20}$ alkyl, $C_{3-20}$ alkenyl, $C_{3-20}$ alkynyl, phenyl, naphthyl, or $C_{7-10}$ phenylalkyl, and each $R_5$, and $R_6$, independently, is any of H, $C_{1-12}$ alkyl, $C_{7-10}$ phenylalkyl, lower acyl, or,

where $R_{22}$ is any of H, $C_{1-12}$ alkyl, $C_{7-10}$ phenylalkyl, or lower acyl; provided that, when one of $R_5$ or $R_6$ is —$NHR_{22}$, the other is H;

(II):

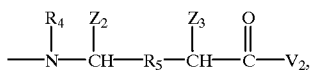

wherein $R_5$ is $CH_2$—NH, $CH_2$—S, $CH_2$—O, CO—$CH_2$, $CH_2$—CO, or $CH_2$—$CH_2$, and each $Z_2$ and $Z_3$, independently, is the identifying group of any one of the amino acids Gly, Ala, Val, Leu, Ile, Ser, Asp, Asn, Glu, Gln, β-Nal, p-X-Phe (where X=H, F, Cl, Br, $NO_2$, OH, or $CH_3$), $F_5$-Phe, Trp, Cys, Met, Pro, HyPro, or CHxAla; and $V_2$ is either $OR_6$ or

where each $R_4$, $R_6$, $R_7$, and $R_8$, independently, is H, lower alkyl, lower phenylalkyl, or lower naphthylalkyl;

(III):

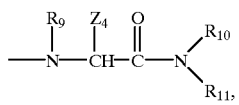

wherein $Z_4$ is the identifying group of any one of the amino acids Gly, Ala, Val, Leu, Ile, Ser, Asp, Asn, Glu, β-Nal, Gln, p-X-Phe (where X=H, F, Cl, Br, $NO_2$, OH, or $CH_3$), $F_5$-Phe, Trp, Cys, Met, Pro, or HyPro; and each $R_9$, $R_{10}$, and $R_{11}$, independently, is H, lower alkyl, lower phenylalkyl, or lower naphthylalkyl; or (IV):

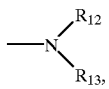

wherein each $R_{12}$ and $R_{13}$, independently, is H, lower alkyl, lower phenylalkyl, lower naphthylalkyl;

provided that, if $A^0$ is present, $A^1$ cannot be pGlu; further provided that, if $A^0$ or $A^1$ is present, $A^2$ cannot be pGlu; further provided that, when $A^0$ is deleted and $A^1$ is pGlu, one of $R_1$ and $R_2$ must be H; further provided that when either of $R_{12}$ or $R_{13}$ is other than H, $A^7$ is His, $A^6$ is Gly, $A^5$ is Val, $A^4$ is Ala, $A^2$ is His, and either of $R_1$ or $R_2$ is other than H, $A^1$ must be other than deleted; and further provided that, for the groups (I) through (IV), any asymmetric carbon atom can be R, S or a racemic mixture; or a pharmaceutically acceptable salt thereof.

Analogs used in the present invention may have one of the modifications given in generic formula (B) above: i.e., either a non-peptide bond (or pseudopeptide bond) instead of a peptide bond between an amino acid residue of the biologically active portion and an adjacent amino acid residue; or a synthetic amino acid, e.g. a statine, an AHPPA, or an ACHPA, a β-amino acid, or a γ-amino acid residue in place of two natural amino acid residues; or a deletion of the C-terminal amino acid residue, accompanied by the addition of a substituent on the actual C-terminal group and the presence of an N-terminal residue that is not the natural N-terminal amino acid residue of the peptides from which the analogs are derived. Statine, AHPPA, and ACHPA have the chemical structures defined above.

By non-peptide bond is meant that the carbon atom participating in the bond between two residues is reduced from a carbonyl carbon to a methylene carbon, i.e., $CH_2$—NH; or, less preferably, that CO-NH is replaced with any of $CH_2$—S, $CH_2$—O, $CH_2$—$CH_2$, $CH_2$—CO, or CO—$CH_2$. In this disclosure, the symbol —ψ[$CH_2NH$]— is used to indicate a non-peptide $CH_2$—NH bond.

A detailed discussion of the chemistry of non-peptide bonds is given in Coy et al. (1988) Tetrahedron 44, 3:835–841, Tourwe (1985) Janssen Chim. Acta 3:3–15, 17–18, and Spatola (1983) in Chemistry and Biochemistry of Amino Acids, Peptides, and Proteins, (B. Weinstein, ed.) Marcel Dekker, New York and Basel, pp. 267–357, all hereby incorporated by reference. The peptide bond reduction method which reduces a carbonyl carbon to a methylene carbon is described in Coy et al., U.S. patent application Ser. No. 879,348, hereby also incorporated by reference. The term "peptide" used herein refers to both traditional peptides and amino acid sequences containing the above described non-peptide bond.

One modification of the naturally occurring peptide to create an analog used in the present invention is of the amino terminal end of the molecule, such as those described for the amino terminal positions in the generic formula (B) above; for example, the N-terminal amino acid residue, which is $A^0$, or if $A^0$ is deleted, is $A^1$, or if $A^0$ and $A^1$ are both deleted, is $A^2$, may be an aromatic D-isomer, or may be an alkylated amino acid residue.

A set of preferred compounds of generic formula (B) includes those in which:

$A^0$=Gly, D-Phe, or is deleted;
$A^1$=p-Glu, D-Phe, D-Ala, D-β-Nal, D-Cpa, or D-Asn;
$A^2$=Gln, His, 1-methyl-His, or 3-methyl-His;
$A^4$=Ala;
$A^5$=Val;
$A^6$=Sar, Gly, D-Phe, or D-Ala;
$A^7$=His;

and, where W is (I) and $R_3$ is $CH_2$ or $CH_2$—$CH_2$, $Z_1$ is the identifying group of Leu or Phe; where W is (I) and $R_3$ is CHOH—$CH_2$, $Z_1$ is the identifying group of Leu, CHxAla, or Phe and each $R_5$ and $R_6$ is H; and where W is (I), $V_1$ is $NHR_6$ and $R_6$ is $NH_2$; where W is (II) and $R_5$ is $CH_2$—NH, each $Z_2$ and $_3$, independently, is the identifying group of Leu or Phe; where W is (III), $Z_4$ is the identifying group of any one of Leu or p-X-Phe (where X=H, F, Cl, Br, $NO_2$, OH, or $CH_3$); and each $R_9$, $R_{10}$ and $R_{11}$, independently, is H, lower alkyl, lower phenylalkyl, or lower naphthylalkyl; and where W is (IV), each $R_{12}$ and $R_{13}$ is H and each $R_1$ and $R_2$, independently, is H, lower alkyl, or lower acyl.

Two particular preferred compounds in this set are:
D-Cpa-Gln-Trp-Ala-Val-Gly-His-Leu-ψ[$CH_2NH$]-Phe-$NH_2$ (code named BIM-26159), and
D-Phe-Gln-Trp-Ala-Val-Gly-His-Leu-ψ[$CH_2NH$]-Cpa-$NH_2$ (code named BIM-26189).

Another set of preferred compounds of generic formula (B) includes those in which $A^0$ is deleted, $A^2$ is Gln, and W is (I) with $R_3$ being deleted and $V_1$ being $OR_4$ where $R_4$ is any of $C_{1-20}$ alkyl, $C_{3-20}$ alkenyl, $C_{3-20}$ alkynyl, phenyl, naphthyl, or $C_{7-10}$ phenylalkyl.

Two particular preferred compounds in this set are
D-Phe-Gln-Trp-Ala-Val-N-methyl-D-Ala-His-Leu-methylester, and
D-$F_5$-Phe-Gln-Trp-Ala-Val-D-Ala-His-Leu-methylester.

In the generic formulae (A) and (B) given above, when either of $R_1$ or $R_2$ is an aliphatic, aromatic, or lipophilic group, the in vivo activity can be long lasting, and delivery of the compounds of the invention to the target tissue can be facilitated.

It is preferred that the therapeutic composition of the invention further includes a pharmaceutically acceptable carrier substance, e.g., mannitol, lactose, magnesium carbonate, or phospholipid with which the peptide can form a micelle.

It is generally the case that peptides such as bombesin analogs are stable at acidic pH, but rapidly degrade under basic conditions and/or in the presence of pancreatic enzymes (trypsin/chymotrypsin). Thus, when given orally, such substances need to be protected against pancreatic enzymes and the intestinal environment (pH and bacteria). Furthermore, a co-transport agent such as glucose might be necessary for oral bioavailability.

Examples of therapeutic compositions that are suitable for oral administration include a pill, tablet, capsule, or liquid. When the composition is administered orally to the subject, it is particularly preferred that the peptide be coated with a substance capable of protecting it from degradation in the subject's stomach for a sufficiently long period of time. This allows all or most of the peptide molecules to pass into and be adsorbed by the small intestine in their intact form.

Alternatively, the therapeutic composition can be prepared in a suitable form, such as a liquid, for administration into the subject via a parenteral route, such as intravenous or subcutaneous administration. Other routes of administration include transdermal (e.g., topical—using cream with or without a penetration enhancer, or iontophoretic) and transmucosal (e.g., nasal, vaginal, buccal or pulmonary). Moreover, targeted delivery to the tumor site by perfusion of the liver can be performed.

The therapeutic composition can also be in the form of a biodegradable sustained release generic formulation suitable for intramuscular administration. For maximum efficacy, zero order release is most preferred. Zero order release can be obtained by means of an implantable or external pump, such as a Zyklomat BT1 Peristaltic pump (Ferring Laboratories, Suffern, N.Y.), to administer the therapeutic composition.

The terms "therapeutically effective amount", "pharmaceutically acceptable salt or complex" and "pharmaceutically acceptable carrier" will be defined respectively below.

Other features and advantages of the invention will be apparent from the following description of the preferred embodiments thereof, and from the claims.

DETAILED DESCRIPTION OF PREFERRED EMBODIMENTS

DRAWING

The drawing will first be briefly described.

STRUCTURE

Figure 1:
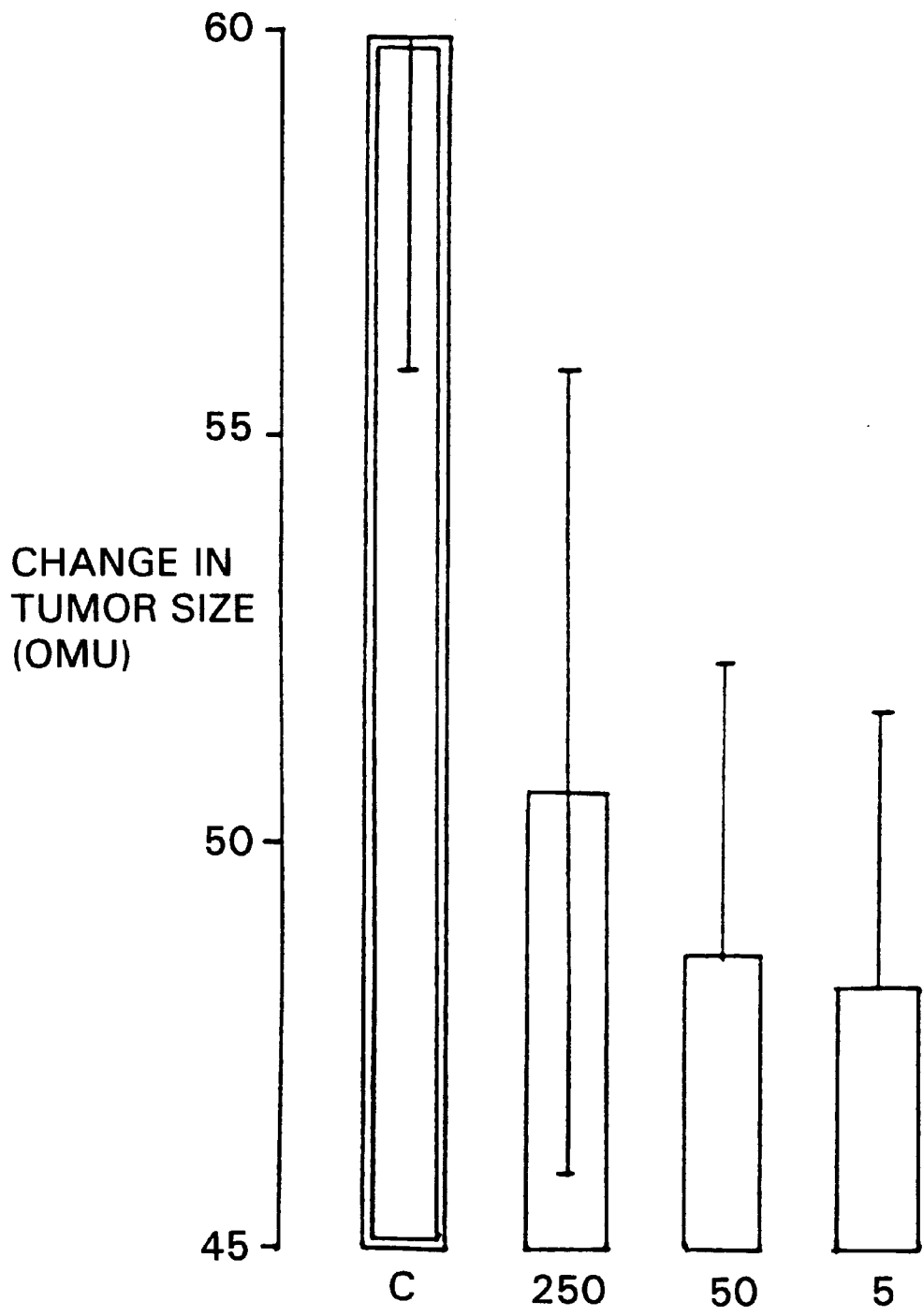
FIG. 1 is a graph showing the growth inhibitory effect of a bombesin analog, BIM-26159, on hepatomas implanted in athymic female mice for 13 days by subrenal capsule assay.

The therapeutic compounds used in the invention have the general structure, i.e., generic formula (A) or (B), recited above in "Summary of the Invention". They are all bombesin analogs containing seven to ten amino acid residues. The term "bombesin analogs" used herein refers to peptides that are derived from, and possess biological activty similar to, one of the peptides which represent the entire sequences, or portions thereof, of naturally-occurring, structurally related peptides, namely, bombesin, neuromedin B, neuromedin C, litorin, and GRP. Relevant amino acid sequences of these naturally occurring peptides are listed below:

Bombesin (last 10 amino acids) A0 A1 A2 A3 A4 A5 A6 A7 A8 A9 Gly-Asn-Gln-Trp-Ala-Val-Gly-His-Leu-Met-$NH_2$
Neuromedin B A0 A1 A2 A3 A4 A5 A6 A7 A8 A9 Gly-Asn-Leu-Trp-Ala-Thr-Gly-His-Phe-Met-$NH_2$
Neuromedin C A0 A1 A2 A3 A4 A5 A6 A7 A8 A9 Gly-Asn-His-Trp-Ala-Val-Gly-His-Leu-Met-$NH_2$
Litorin:
A1 A2 A3 A4 A5 A6 A7 A8 A9 pGlu-Gln-Trp-Ala-Val-Gly-His-Phe-Met-$NH_2$
Human GRP (last 10 amino acids) A0 A1 A2 A3 A4 A5 A6 A7 A8 A9 Gly-Asn-His-Trp-Ala-Val-Gly-His-Leu-Met-$NH_2$ Analogs used in the invention are described in (1) Coy et al., U.S. patent application Ser. No. 502,438, filed Mar. 30, 1990, which is a continuation-in-part of U.S. patent application Ser. No. 397,169, filed Aug. 21, 1989, which is a continuation-in-part of U.S. patent application Ser. No. 376,555, filed Jul. 7, 1989, and U.S. patent application Ser. No. 394,727, filed Aug. 16, 1989, both of which are continuation-in-parts of U.S. patent application Ser. No. 317,941, filed Mar. 2, 1989, which is a continuation-in-part of U.S. patent application Ser. No. 282,328, filed Dec. 9, 1988, which is a continuation-in-part of U.S. patent application Ser. No. 257,998, filed Oct. 14, 1988, which in turn is a continuation-in-part of U.S. patent application Ser. No. 248,771, filed Sep. 23, 1988, which in turn is a continuation-in-part of Coy et al., U.S. patent application Ser. No. 207,759, filed Jun. 16, 1988, which in turn is a continuation-in-part of Coy et al., U.S. patent application Ser. No. 204,171, filed Jun. 8, 1988, which in turn is a continuation-in-part of Coy et al., U.S. patent application Ser. No. 173,311, filed Mar. 25, 1988, which in turn is a continuation-in-part of Coy et al. U.S. patent application Ser. No. 100,571, filed Sep. 24, 1987; and (2) Bogden, et al., U.S. patent application Ser. No. 520,225, filed May 9, 1990, which in turn is a continuation-in-part of Bogden et al. U.S. patent application Ser. No. 440,039, filed Nov. 21, 1989. All these applications are assigned to the same assignee and hereby incorporated by reference.

Bombesin analogs are also described in Zachary et al., Proc. Nat. Aca. Sci. 82:7616 (1985); Heimbrook et al., "Synthetic Peptides: Approaches to Biological Problems", UCLA Symposium on Mol. and Cell. Biol. New Series, Vol. 86, ed. Tam and Kaiser; Heinz-Erian et al., Am. J. Physiol. G439 (1986); Martinez et al., J. Med. Chem. 28:1874 (1985); Gargosky et al., Biochem. J. 247:427 (1987); Dubreuil et al., Drug Design and Delivery, Vol 2:49, Harwood Academic Publishers, GB (1987); Heikkila et al., J. Biol. Chem. 262:16456 (1987); Caranikas et al., J. Med. Chem. 25:1313 (1982); Saeed et al., Peptides 10:597 (1989); Rosell et al., Trends in Pharmacological Sciences 3:211 (1982); Lundberg et al., Proc. Nat. Aca. Sci. 80:1120, (1983); Engberg et al., Nature 293:222 (1984); Mizrahi et al., Euro. J. Pharma. 82:101 (1982); Leander et al., Nature 294:467 (1981); Woll et al., Biochem. Biophys. Res. Comm. 155:359 (1988); Rivier et al., Biochem. 17:1766 (1978); Cuttitta et al., Cancer Surveys 4:707 (1985); Aumelas et al., Int. J. Peptide Res. 30:596 (1987); all of which are also hereby incorporated by reference.

The analogs can be provided in the form of pharmaceutically acceptable salts, e.g., acid addition salts, or metal complexes, e.g., with zinc, iron or the like. Illustrative examples of acid addition salts are those with organic acids such as acetic, lactic. pamoic, maleic, citric, malic, ascorbic, succinic, benzoic, salicylic, tartric, methanesulfonic or toluenesulfonic acid, those with polymeric acids such as tannic acid or carboxymethyl cellulose, and those with inorganic acids such as hydrochloric acid, hydrobromic acid, sulfuric acid or phosphoric acid.

Synthesis of Analogs

The synthesis of the bombesin analog pGlu-Gln-Trp-Ala-Val-Gly-His-Leu-ψ [$CH_2NH$]-Leu-$NH_2$ follows. Other bombesin analogs were prepared by making appropriate modifications of the following synthetic method.

The first step was the preparation of the intermediate, pGlu-Gln-Trp-Ala-Val-Gly-His (benzyloxycarbonyl)-Leu-ψ [$CH_2NH$]-Leu-benzhydrylamine resin, as follows.

Benzhydrylamine-polystyrene resin (Vega Biochemicals, Inc.) (0.97 g, 0.5 mmole) in the chloride ion form was placed in the reaction vessel of a Beckman 990B peptide synthesizer programmed to perform the following reaction cycle:

(a) methylene chloride; (b) 33% trifluoroacetic acid (TFA) in methylene chloride (2 times for 1 and 25 min. each); (c) methylene chloride; (d) ethanol; (e) methylene chloride; and (f) 10% triethylamine in chloroform.

The neutralized resin was stirred with -t-butoxycarbonyl ("BOC")-Leu and diisopropylcarbodiimide (1.5 mmole each) in methylene chloride for 1 hour, and the resulting amino acid resin was then cycled through steps (a) to (f) in the above wash program. BOC-Leu aldehyde (1.25 mmoles), prepared by the method of Fehrentz and Castro, Synthesis, p. 676 (1983), was dissolved in 5 ml of dry dimethylformamide (DMF) and added to the resin TFA salt suspension followed by the addition of 100 mg (2 mmoles) of sodium cyanoborohydride [Sasaki and Coy, Peptides 8:119–121 (1987); Coy et al., Id.]. After stirring for 1 hour, the resin mixture was found to be negative to ninhydrin reaction (1 min.), indicating complete derivatization of the free amino group.

The following amino acids (1.5 mmole) were then coupled successively in the presence diisopropylcarbodiimide (1.5 mmole), and the resulting amino acid resin was cycled through washing/deblocking steps (a) to (f) in the same procedure as above: BOC-His(benzyloxycarbonyl), BOC-Gly (coupled as a 6 M excess of the p-nitrophenylester), BOC-Val, BOC-Ala, BOC-Trp, BOC-Gln (coupled as a 6 M excess of the p-nitrophenylester), and pGlu. The completed resin was then washed with methanol and air dried.

The resin described above (1.6 g, 0.5 mmole) was mixed with anisole (5 ml) and anhydrous hydrogen fluoride (35 ml) at 0° C. and stirred for 45 min. Excess hydrogen fluoride was evaporated rapidly under a stream of dry nitrogen, and free peptide was precipitated and washed with ether. The crude peptide was dissolved in a minimum volume of 2 M acetic acid and eluted on a column (2.5×100 mm) of Sephadex G-25 (Pharmacia Fine Chemicals, Inc.). Fractions containing a major component by UV absorption and thin layer chromatography (TLC) were then pooled, evaporated to a small volume and applied to a column (2.5×50 cm) of octadecylsilane-silica (Whatman LRP-1, 15–20 μm mesh size).

The peptide was eluted with a linear gradient of 0–30% acetonitrile in 0.1% trifluoroacetic acid in water. Fractions were examined by TLC and analytical high performance liquid chromatography (HPLC) and pooled to give maximum purity. Repeated lyophilization of the solution from water gives 60 mg of the product as a white, fluffy powder.

The product was found to be homogeneous by HPLC and TLC. Amino acid analysis of an acid hydrolysate confirms the composition of the peptide. The presence of the Leu-ψ [CH$_2$—NH]-Leu bond was demonstrated by fast atom bombardment mass spectrometry.

pGlu-Gln-Trp-Ala-Val-Gly-His-Phe-ψ [CH$_2$NH]-Leu-NH$_2$, pGlu-Gln-Trp-Ala-Val-Gly-His-Leu-ψ [CH$_2$NH]-Leu-NH$_2$, pGlu-Gln-Arg-Leu-Gly-Asn-Gln-Trp-Ala-Val-Gly-D-Phe-Leu-Met-NH$_2$, pGlu-Gln-Arg-Leu-Gly-Asn-Gln-Trp-Ala-Val-Gly-D-Phe-Leu-Leu-NH$_2$, pGlu-Gln-Arg-Tyr-Gly-Asn-Gln-Trp-Ala-Val-Gly-D-Phe-Leu-Met-NH$_2$, or other peptides were prepared in similar yields in an analogous fashion by appropriately modifying the above procedure.

Solid phase synthesis of D-Phe-Gln-Trp-Ala-Val-Gly-His-Leu-ψ [CH$_2$NH]-D-Phe-NH$_2$, was carried out as follows:

BOC-D-Phe-Gln-Trp-Ala-Val-Gly-His(tosyl)-Leu-ψ [CH$_2$NH]-D-Phe-benzhydrylamine resin was synthesized first.

Benzhydrylamine-polystyrene resin (Advanced ChemTech, Inc.) (1.25 g, 0.5 mmole) in the chloride ion form was placed in the reaction vessel of an Advanced ChemTech ACT 200 peptide synthesizer programmed to perform the following reaction cycle: (a) methylene chloride; (b) 33% trifluoroacetic acid in methylene chloride (2 times for 1 and 25 min. each); (c) methylene chloride; (d) ethanol; (e) methylene chloride; (f) 10% triethylamine in chloroform.

The neutralized resin was stirred with BOC-D-phenylalanine and diisopropylcarbodiimide (1.5 mmole each) in methylene chloride for 1 hour and the resulting amino acid resin was then cycled through steps (a) to (g) in the above wash program. The BOC group was then removed by TFA treatment. BOC-Leu aldehyde (1.25 mmoles), prepared by the method of Fehrentz and Castro, Id., was dissolved in 5 ml of dry DMF and added to the resin TFA salt suspension followed by the addition of 100 mg (2 mmoles) of sodium cyanoborohydride. After stirring for 1 hour, the resin mixture was found to be negative to ninhydrin reaction (1 min.) indicating complete derivatization of the free amino group.

The following amino acids (1.5 mmole) were then coupled successively by the same procedure: BOC-His (benzyloxycarbonyl), BOC-Gly, BOC-Val, BOC-Ala, BOC-Trp, BOC-Gln (coupled in the presence of 1 equiv. hydroxybenzotriazole), BOC-D-Phe (coupled in the presence of 1 equiv. hydroxybenzotriazole). After drying, the peptide resin weighed 1.93 g.

The resin (1.93 g, 0.5 mmole) was mixed with anisole (5 ml) and anhydrous hydrogen fluoride (35 ml) at 0° C. and stirred for 45 min. Excess hydrogen fluoride was evaporated rapidly under a stream of dry nitrogen and free peptide precipitated and washed with ether. The crude peptide was dissolved in a minimum volume of 2 M acetic acid and eluted on a column (2.5×100 mm) of Sephadex G-25. Fractions containing a major component by UV absorption and TLC were then pooled, evaporated to a small volume and applied to a column (2.5×50 cm) of Vydac octadecylsilane (10–15 uM). This was eluted with a linear gradient of 15–45% acetonitrile in 0.1% trifluoroacetic acid in water. Fractions were examined by TLC and analytical HPLC and pooled to give maximum purity. Repeated lyophilization of the solution from water gives 120 mg of the product as a white, fluffy powder.

The product was found to be homogeneous by HPLC and tlc. Amino acid analysis of an acid hydrolysate confirms the composition of the peptide. The presence of the Leu-ψ [CH$_2$NH] peptide bond was demonstrated by fast atom bombardment mass spectrometry.

The analog D-Cpa-Gln-Trp-Ala-Val-Gly-His-Leu-ψ [CH$_2$NH]-Phe-NH$_2$ (BIM-26159) may be synthesized in a similar manner by substituting D-Cpa for D-Phe.

Solid phase synthesis of [D-Phe[1], His[7], desMet[9]] Litorin, D-Phe-Gln-Trp-Ala-Val-Gly-His-Leu-NH$_2$, was carried out as follows.

Step (1): Benzhydrylamine-polystyrene resin (Advanced ChemTech, Inc. (0.62 gm, 0.25 mmole) in the chloride ion form was placed in the reaction vessel of an ACT 200 peptide synthesizer programmed to perform the following reaction cycle: (a) methylene chloride; (b) 33% trifluoroacetic acid in methylene chloride (2 times for 1 and 25 min. each); (c) methylene chloride; (d) ethanol; (e) methylene chloride; (f) 10% triethylamine in chloroform.

The neutralized resin was stirred with BOC-Leu and diisopropylcarbodiimide (1.5 mmole each) in methylene chloride for 1 hour and the resulting amino acid resin was then cycled through steps (a) to (g) in the above wash program. The following amino acids (1.5 mmole) were then coupled successively by the same procedure: BOC-His (benzyloxycarbonyl), BOC-Gly, BOC-Val, BOC-Ala, BOC-Trp, BOC-Gln (coupled as a 6M excess of the p-nitrophenylester, and BOC-D-Phe (coupled in the presence of hydroxzybenzotriazole). After drying, the peptide resin weighed 0.92 g.

Step (2): The resin (0.92 g) was then mixed with anisole (5 ml), dithiothreitol (200 mg) and anhydrous hydrogen fluoride (35 ml) at 0° C. and stirred for 45 min. Excess hydrogen fluoride was evaporated rapidly under a stream of dry nitrogen and free peptide precipitated and washed with ether. The crude peptide was dissolved in a minimum volume of 2 M acetic acid and eluted on a column (2.5×100 cm) of Sephadex G-25. Fractions containing a major component by UV absorption and TLC were then pooled, evaporated to a small volume and applied to a column (2.5×50 cm) of Vydac octadecylsilane (10–15 microM). The column was eluted with a linear gradient of 0–30% acetonitrile in 0.1% trifluoroacetic acid in water. Fractions were examined by TLC and pooled to give maximum purity. Repeated lyophilization of the solution from water gives a white, fluffy powder; this product was found to be homogeneous by HPLC and TLC. Amino acid analysis of an acid hydrolysate confirms the composition of the peptide.

Synthesis of D-P-Nal-Gln-Trp-Ala-Val-Gly-His-Leu-NH$_2$ was accomplished using the same procedure as described above [0.62 g, 0.25 mmole of benzyhydrylamine resin in step (1), and 0.92 g in step (2))]

Synthesis of N-acetyl-D-Phe-Gln-Trp-Ala-Val-Gly-His-Leu-NH$_2$ was accomplished using the same procedure as that described above, using 0.62 g (0.25 mmole) of benzhydrylamine resin in step (1), and mixing 0.92 g of the resin with anisole in step(2), except that the final BOC group was removed and the resin acetylated with acetic anhydride in methylene chloride.

The synthesis of [Sta$^8$, desMet$^9$] Litorin follows. A statine, AHPPA, or ACHPA residue was substituted in place of any two amino acids of the analog, where the peptide contains only peptide bonds. For example, [Sta$^8$, desMet$^9$] Litorin was prepared in an analogous fashion by first coupling statine to the resin and then proceeding with the addition of BOC-His(benzylocarbonyl).

Statine or BOC-statine was synthesized according to the method of Rich et al., 1978, J. Organic Chem. 43; 3624; and Rich et al., 1980, J. Med. Chem. 23: 27, and AHPPA and ACHPA were synthesized according to the method of Hui et al., 1987, J. Med. Chem. 30: 1287; Schuda et al., 1988, J. Org. Chem. 53:873; and Rich et al., 1988, J. Org. Chem. 53:869.

Solid-phase synthesis of the peptide pGlu-Gln-Trp-Ala-Val-Gly-His-Sta-NH$_2$ was accomplished through the use of the following procedures in which BOC-statine (prepared by the procedure of Rich et al., J. Org. Chem. 1978, 43, 3624) was first coupled to methyl-benzhydrylamine-polystyrene resin. After acetylation, the intermediate p-Glu-Gln-Gln-Trp-Ala-Val-Gly-His(benzyloxycarbonyl)-Sta-methylbenzhydrylamine resin was prepared. The synthetic procedure used for this preparation follows in detail:
1. Incorporation of BOC-statine on Methylbenzhydrylamine Resin Methylbenzhydrylamine-polystyrene resin (Vega Biochemicals, Inc.) (1.0 g, 0.73 mmol) in the chloride ion form was placed in the reaction vessel of a Vega 250C Coupler peptide synthesizer. The synthesizer was programmed to perform the following reactions: (a) methylene chloride; (b) 10% triethylamine in chloroform; (c) methylene chloride; and (d) dimethylformamide.

The neutralized resin was mixed for 18 hours with the preformed active ester made from BOC-statine (1.46 mmol), diisopropyl carbodiimide (2 mmol), and hydroxybenzotriazole hydrate (1.46 mmol in dimethylformamide at 0° C. for one hour. The resulting amino acid resin was washed on the synthesizer with dimethylformamide and then methylene chloride. The resin mixture at this point was found by the Kaiser ninhydrin test (5 min.) to have an 84% level of statine incorporation on the resin.

Acetylation was performed by mixing the amino acid-resin for 15 min. with N-acetyl imidazole (5 mmol) in methylene chloride. Derivatization to the 94–99% level of the free amino groups of the resin was indicated by the Kaiser ninhydrin test (5 min.). The BOC-statine-resin was then washed with methylene chloride.
2. Couplings of the Remaining Amino Acids The peptide synthesizer was programmed to perform the following reaction cycle: (a) methylene chloride; (b) 33% trifluoroacetic acid (TFA) in methylene chloride (2 times for 5 and 25 min. each); (c) methylene chloride; (d) isopropyl alcohol; (e) 10% triethylamine in chloroform; and (f) ethylene chloride.

The following amino acids (2.19 mmol) were then coupled successively by diisopropyl carbodiimide (4 mmol) alone or diisopropyl carbodiimide (4 mmol) plus hydroxybenzotriazole hydrate (1.47 or 0.73 mmol) and the resulting peptide-resin was washed on the synthesizer with dimethylformamide and then methylene chloride, and then cycled through the washing and deblocking steps (a) to (f) in the procedure described above.

BOC-His (benzyloxycarbonyl) (coupled in the presence of 2 equivalents hydroxybenzotriazole); BOC-Gly; BOC-Val; BOC-Ala and BOC-Trp (coupled as the preformed hydroxybenzotriazole active esters made by reaction at 0° C. for one hour with 1 equivalent hydroxybenzotriazole hydrate); BOC-Gln and pGlu (also coupled as the preformed active esters of hydroxybenzotriazole made by reaction at 0° C. for one hour with 1 equivalent hydroxybenzotriazole hydrate). The completed peptide-resin was then washed with methanol and air dried.

The peptide-resin described above (1.60 g, 0.73 mmol) was mixed with anisole (2.5 ml), dithioerythreitol (50 mg), and anhydrous hydrogen fluoride (30 ml) at 0° C. for one hour. Excess hydrogen fluoride was evaporated rapidly under a stream of dry nitrogen, and the free peptide was precipitated and washed with ether. The crude peptide was dissolved in 100 mL of 1 M acetic acid and the solution was then evaporated under reduced pressure. The crude peptide was dissolved in a minimum volume of methanol/water 1/1 and triturated with 10 volumes of ethyl acetate.

The triturated peptide was applied to a column (9.4 mm I.D. × 50 cm) of octadecylsilane-silica (Whatman Partisil 10 ODS-2 M9). The peptide was eluted with a linear gradient of 20–80% of 20/80 0.1% trifluoroacetic acid/acetonitrile in 0.1% trifluoroacetic acid in water. Fractions were examined by TLC and analytical HPLC and pooled to give maximum purity. Lyophilization of the solution from water gives 77 mg of the product as a white fluffy powder.

The synthesis of the bombesin analog, D-Phe-Gln-Trp-Ala-Val-Gly-His-Leu-Leu-NH$_2$ (BIM-26187), follows. Other bombesin analogs were prepared by making appropriate modifications of the following synthetic method. 1) Incorporation of BOC-Leu on 4-methyl benzhydrylamine.

4-methyl benzhydrylamine-polystyrene resin (Bachem, Inc.) (0.72 meq/g) in the chloride ion form was placed in the reaction vessel of an ACT200 peptide synthesizer (Advanced Chem Tech, Inc.) programmed to perform the following reaction cycle: (a) methylene chloride; (b) 10% triethylamine in chloroform; (c) methylene chloride; and (d) dimethylformide.

The neutralized resin was mixed with BOC-Leu and diisopropylcarbodiimide (3 molar eq. each) in methylene chloride for 1 hour. The resulting amino acid resin was washed on the synthesizer with dimethyl-formamide and treated with 5% acetic anhydride in dimethylformamide for 5 min. Then it was washed with dimethylformamide and methylene chloride.

2) Couplings of the remaining amino acids

The peptide synthesizer was programmed to perform the following reaction cycle: (a) methylene chloride; (b) 33% trifluoroacetic acid (TFA) in methylene chloride (2 times for 5 and 25 min. each); (c) methylene chloride; (d) isopropyl alcohol; (e) 10% triethylamine in chloroform; and (f) methylene chloride.

The following amino acids (3 molar eq.) were then coupled successively by the same procedure: BOC-Leu, BOC-His (tosyl), BOC-Gly, BOC-Val, BOC-Ala, BOC-Trp, BOC-Gln (coupled in the presence of 1 eq. hydroxybenzotriazole), BOC-D-Phe (coupled in the presence of 1 eq. hydroxybenzotriazole). The completed resin was then washed with methanol and air dried.

The peptide resin described above (1.41 g) was mixed with anisole (5 ml), dithioerythreitol (50 mg), and anhydrous hydrogen fluoride (25 ml) at 0° C. for one hour. Excess hydrogen fluoride was evaporated rapidly under a stream of dry nitrogen, and the residue was washed in ether. Crude peptide was dissolved in 100 ml of 4 M acetic acid and the solution was then evaporated under reduced pressure. The crude peptide was dissolved in minimum volume of methanol/water and triturated with ethyl acetate. The triturated peptide was applied to a column (9.4 mm I.D.× 50 cm) of octadecylcilane-silica (Whatman Partisil 10 ODS—2M9). The peptide was eluted with a linear gradient of 20–80% of 50/50 0.1% TFA/acetonitrile in 0.1% TFA in water. Fractions were examined by analytical HPLC and appropriate fractions were evaporated to a small volume, which was further lyophilized, gives 65 mg of the product as a colorless powder.

Other compounds including [D-Cpa$^1$, β-Leu$^8$, desMet$^9$] Litorin, or compounds containing, e.g., CHxAla$^8$ or Nle$^9$, were prepared as above; a statine, AHPPA, ACHPA, β-amino acid, or γ-amino acid residue was added in the same way as was a natural -amino acid residue, by coupling as a BOC derivative.

Resins used for peptide synthesis were selected according to the chemical structure of the C-terminus of the peptide. More specifically, Merrifield resin was coupled to the first amino acid by an ester bond which, upon cleavage, yielded a carboxyl C-terminus; methylbenzhydrylamine and benzylhydrylamine resins, on the other ahnd, were coupled to the first amino acid by a secondary amine bond which, upon cleavage, yielded an amide C-terminus.

Peptides modified at their C-terminal end were prepared by appropriate modifications of the procedure described above. For example, 0-methyl ester derivatives was synthesized as described in Camble et al., "ICI 216140 A Potent In Vivo Antagonist Analogue of Bombesin/Gastrin Releasing Peptide Derived From the C-Terminal Sequence Lacking the Final Methionine Residue", Life Science, Oct.–Nov. 1989, hereby incorporated by reference.

Camble et al. describe the synthesis of an analog of bombesin having a trimethylacetyl-modified N-terminus and a methyl-ester modified C-terminus. This analog, $(CH_3)_3C$-CO-His-Trp-Ala-Val-D-Ala-His-Leu-OCH$_3$, was synthesized by solid phase methods, as described above. The N-terminal trimethylacetyl modification can be obtained by reaction of the corresponding anhydrides with the peptide. The C-terminal methyl ester modification can be obtained by treating the peptide resin with methanol and triethylamine.

Peptides of the invention may be cyclized by formation of disulfide bridges if there are two cysteine residues present in the peptide, or according to a procedure set forth in the following example if in the absence of a Cys—Cys disulfide linkage.

Crude peptide acid obtained from peptide-resin ester by HF cleavage was dissolved in DMF (0.1%–1% concentration), treated with condensing agent (e.g., BOP reagent, DEPC reagent, DPPA reagent, or any other condensing agent) followed by base (e.g., triethylamine, diisopropylethylamine) at room temperature for 1–3 days. After the solvent was removed in vacuum to dryness, the residue was purified by HPLC according to conventional procedures. The cyclization of cyclo[D-Phe$^1$, Leu$^8$, Leu$^9$] Litorin, in which D-Phe$_1$ was covalently linked to Leu$^9$ through an amide bridge, was accomplished according to the above procedure using benzotriazol-1-yloxytris (dimethylamine)phosphonium hexafluorophosphate as the BOP reagent, diethylcyanophosphonate as the DEPC reagent, and diphenylphosphoryalazide as the DPPA reagent.

Determination of Anti-HeDatoma Activity of Analogs

Tumor System

The M5123 hepatoma cells, obtained from Dr. H. P. Morris at the National Cancer Institute, were induced in the Buffalo strain of rats by ingestion of N-(2-fluorenyl-phthalamic acid) and established in serial transplantation. Implantation of the M5123 hepatoma cells in an immuno-deficient athymic mouse reproducibly results in progressively growing, lethal tumor.

Assay System

To determine the growth inhibitory effect of bombesin analogs on hepatoma cells, two in vivo assay systems, the subrenal capsule assay and the subcutaneous tumor assay, were employed.

(1) Subrenal Capsule Assay

Subrenal capsule assay was designed as a rapid in vivo method for testing chemotherapeutic agents against tumor xenografts prepared from solid malignancies. As an antitumor screening procedure, tumors, both human and murine, can be tested as xenografts in athymic female mice. For detailed description of this assay, see Bogden, A.E. et al. A rapid screening method for testing chemotherapeutic agents against human tumor xenografts. In: Proc. Symp. Use of Athymic (Nude) Mice in Cancer Research, p. 231, Edited by Houchens et al., Gustav Fisher, N.Y. (1978).

Fundamental to its design were the considerations that solid tumors are composed of heterogeneous cell populations (heterogeneous in terms of biosynthetic functions, growth potential, drug and growth factor sensitivity, and expression of antigens or receptors), and that the complexity of epithelial/stromal relationship not only affects tumor growth, but also affects other functional characteristics as well.

By utilizing tumor fragments for subrenal capsule implantation, the integrity of both cell membrane which are essential for receptor reactions, cell-to-cell contact and the spatial relationship of the cell populations, and tissues within the tumor fragments which are essential for the stability of autocrine and paracrine effects are maintained. Tumor response to drug or biological response modifier, such as a bombesin analog, in such a relatively intact microenvironment is measured as a net response of multiple cell populations, both clonogenic and non-clonogenic. It also more realistically provides the accessibility barriers of the existing intercellular environment.

Further, an in situ determination of tumor xenograft size at the time of implantation and again at termination of the experiment, permits use of the very simple parameter of change in tumor size for evaluating tumor sensitivity to the teat compounds. Since the initial measurement provides each xenograft with its own baseline for evaluating drug effects, one can measure tumor response to drugs in terms of progression, quiescence, partial remission and complete remission, all of which are parameters that have clinical relevance.

In this assay, xenografts prepared from the transplantation-established M5123 hepatoma were first implanted in immunodeficient athymic female mice, followed by treatment with a bombesin analog, BIM-26159. More specifically, thirty two athymic female mice were implanted under the renal capsule with 1 mm cubed grafts of the M5123 rat hepatoma on day zero. Treatment with BIM-26159 was initiated on day one at 250, 50 and 5 $\mu$g per injection, s.c., b.i.d., on a q.d. 1–12 schedule. On day 13, the mice were sacrificed, the kidney was removed and the size of the tumor was measured to determine changes in tumor size between day 0 and day 13.

The size of the tumor was measured in situ by means of a stereoscope, which was fitted with an ocular micrometer calibrated in ocular units (OMU, 10 OMU=1 mm). For each tumor, two perpendicular diameters were measured and the difference in mean tumor diameter over the 13-day period was calculated.

(2) Subcutaneous Assay

In contrast to the subrenal capsule assay, in the subcutaneous assay, tumor xenografts are implanted subcutaneously, rather than under the subrenal capsule, and treatment can be initiated at any selected time after the implantation.

In this assay, tumors were implanted subcutaneously in the right flank of athymic female mice and test compounds, BIM-26159, BIM-26187, BIM-26189, BIM-26218, BIM-26223 and BIN-26228, and control were injected subcutaneously in the left flank. For the structures of BIM-26159, BIM-26187, BIM-26189, see "Summary of the Invention" above. The structures of BIM-26223 and BIM-26228 are as follows:

BIM-26223: D-Phe-Gln-Trp-Ala-Val-Gly-His-Phe-Leu-NH$_2$

BIM-26228 D-Phe-Gln-Trp-Ala-Val-Gly-CHxAla-Leu-NH$_2$

Response of an implanted tumor to the treatment was monitored as follows. The length and width of the tumor were first measured using sensitive Vernier calipers. Tumor weight was then calculated based on the measurements as follows: [length (mm)×width (mm)$^2$]/2 mg. In addition to tumor size or weight, this assay system permits the parameter of "lag time", i.e., the effect of early treatment on the growth potential of tumors to reach a certain size.

In one experiment, thirty two mice were implanted subcutaneously with M5123 hepatoma xenografts on day 0 and randomized into four groups of eight animals per group. The bombesin analog BIM-26159 was administered at 250, 50, 10 $\mu$g per injection, S.C., b.i.d.,q.d. 1–18.

In another experiment, we tested the activity of five bombesin analogs, i.e., BIM-26187, BIM-26189, BIM-26218, BIM-26223 and BIM-26228, over a period of 18 days. Forty mice were implanted s.c. with M5123 hepatoma xenografts on day 0, and the randomized into ten animals in the control group and six animals per test group. All compounds were administered at 100 $\mu$g per injection, s.c., b.i.d., q.d. 1–18.

Results

Shown in FIG. 1 are the effects of BIM-26159, determined by the subrenal capsule assay, on the growth of hepatoma cells implanted in athymic female mice. At all three dosages tested, i.e., 5, 50 and 250 $\mu$g/injection, s.c., b.i.d., q.d. 1–9, this bombesin analog effected a significant reduction, namely about 20% (i.e., [100—% Test/Control] %), in the growth of the liver tumor over a period of 13 days. It is noteworthy that such effect was observed when the dosage was as low as 5 $\mu$g per injection. The same results are also shown in Table 1.

TABLE 1

| Treatment | Change in Tumor Size[1] (omu) | % Test/Control[2] |
|---|---|---|
| Saline vehicle control, 0.2 ml., s.c., q.d. 1-12 | 59.87 ± 4.05 | — |
| BIM-26159, 250 $\mu$g/inj., s.c., b.i.d., q.d. 1-12 | 50.63 ± 5.22 | 84 |
| BIM-26159, 50 $\mu$g/inj., s.c., b.i.d., q.d. 1-12 | 48.62 ± 3.80 | 81 |
| BIM-26159, 5 $\mu$g/inj., s.c., b.i.d., q.d. 1-12 | 48.19 ± 3.37 | 80 |

[1] Data reported as means ± s.e.m. on 8 animals in control and test groups.
[2] % Test/Control = Test tumor size/Control tumor size × 100

Figure 2:
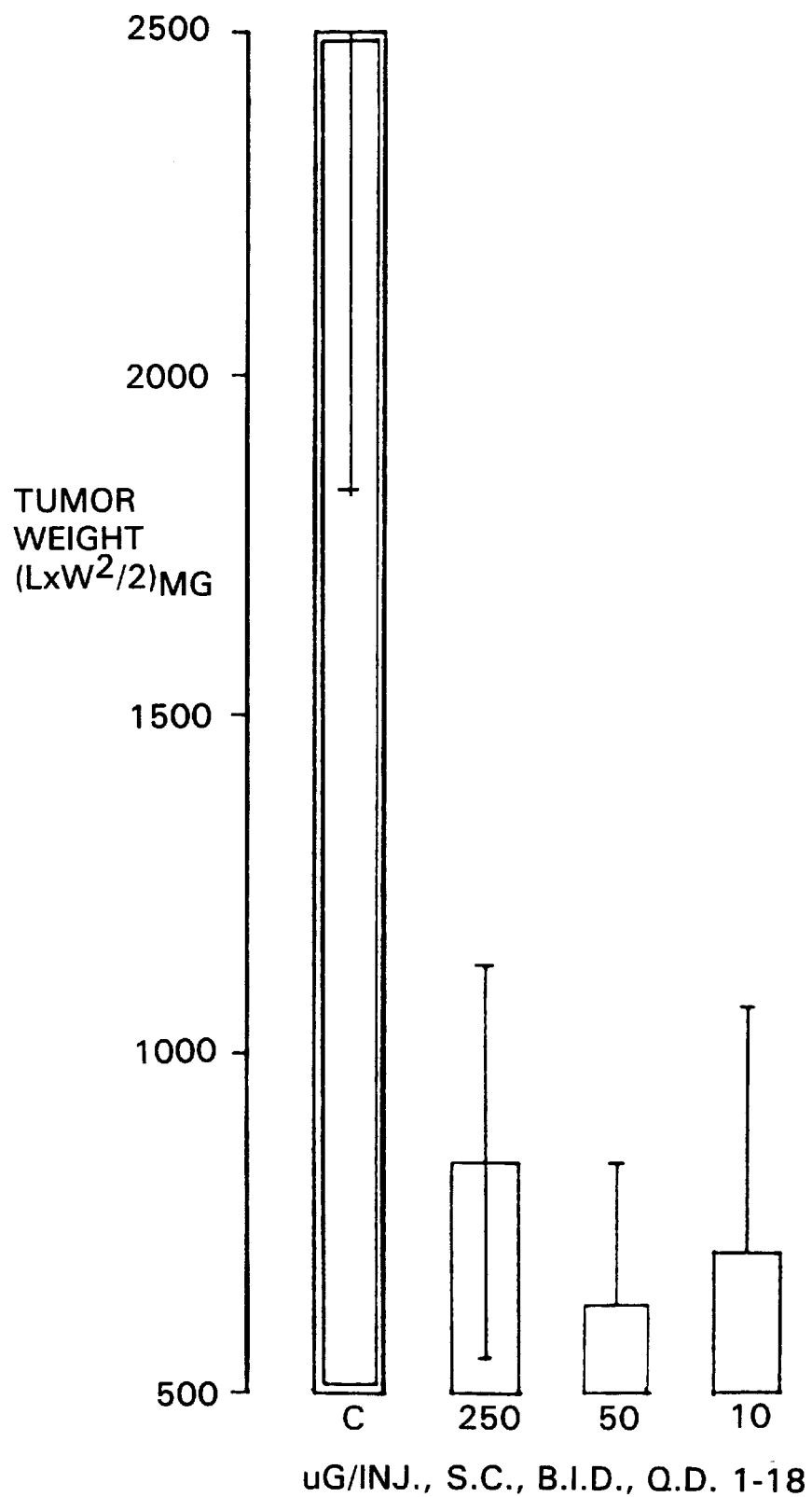
FIG. 2 is a graph showing the growth inhibitory effect of BIM-26159 on hepatomas implanted in athymic female mice for 18 days by subcutaneous assay.
Figure 3:
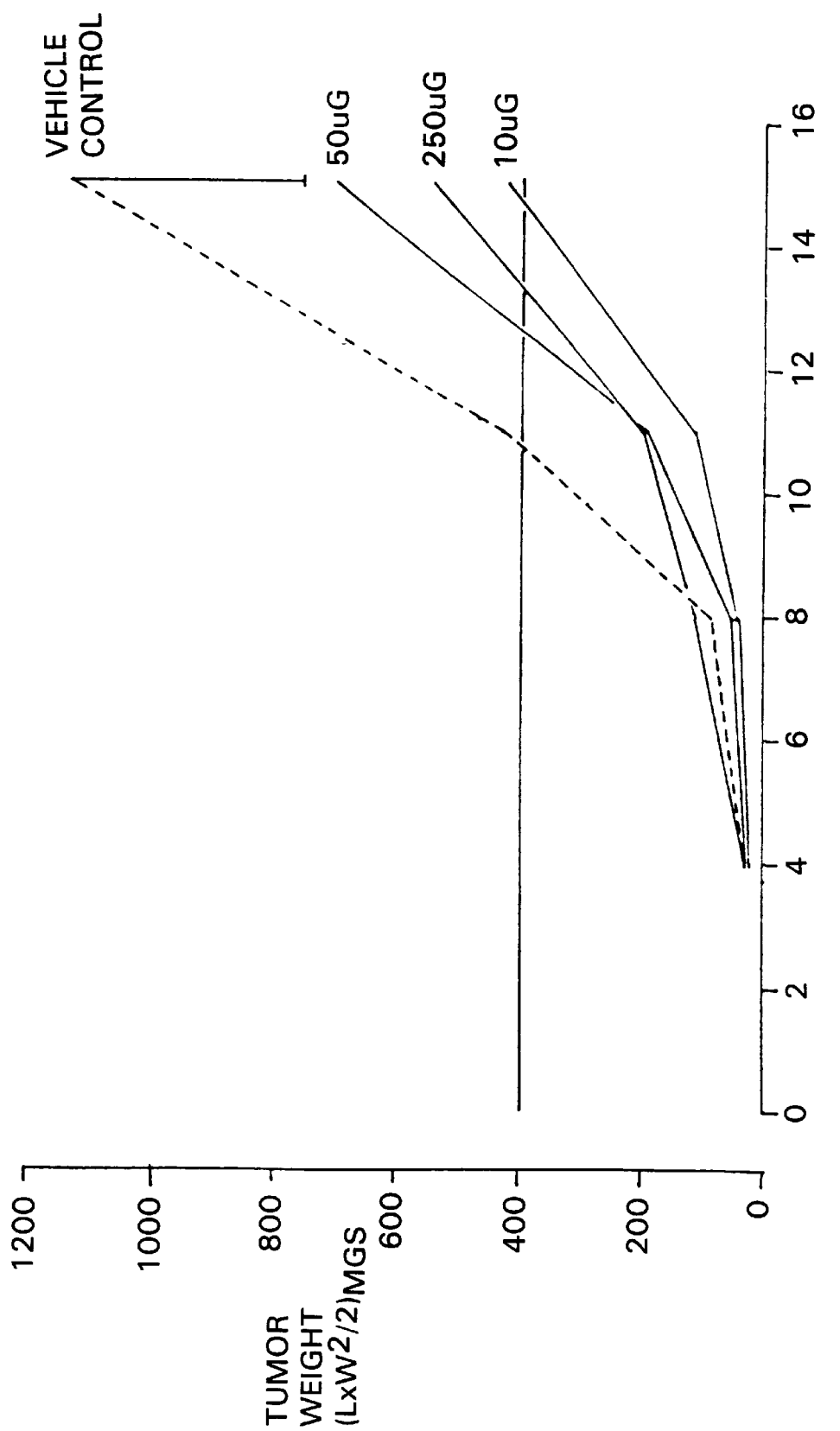
FIG. 3 is a graph showing the growth inhibitory effect of BIM-26159 at various time points on hepatomas implanted in athymic female mice by subcutaneous assay.

The growth inhibitory effect of BIM-26159 was much more pronounced when the subcutaneous assay was employed. As shown in both FIG. 2 and Table 2, this bombesin analog, at various dosages, greatly reduced the growth of hepatoma cells. At a dosage of 50 $\mu$g per injection, s.c., b.i.d., q.d. 1–9, it effected a 75% reduction in the growth of the tumor over a period of 18 days. BIM-26159 administered at a lower dose (10 $\mu$g) and at a higher dose (250 $\mu$g) exhibited slightly less antitumor activity (72% and 66% inhibition, respectively), producing an inverted bell-shaped dose response (FIG. 2). In the same experiment, the growth of the implanted tumor was also monitored at various time points, i.e., day 4, day 8, day 11 and day 15. As clearly shown in FIG. 3, the growth rate of the implanted tumor was much lower upon treatment with BIM-26159 at all three dosages after day 8, as compared with the control.

TABLE 2

| Treatment | Tumor Weight[1] Day 18 (mg) | % Test/Control[2] |
|---|---|---|
| Saline vehicle control, 0.2 ml, s.c., q.d. 1-18 | 2847 ± 652 | — |
| BIM-26159, 250 $\mu$g/inj., s.c., b.i.d., q.d. 1-18 | 838 ± 289 | 34 |
| BIM-26159, 50 $\mu$g/inj., s.c., b.i.d., q.d. 1-18 | 633 ± 204 | 25 |
| BIM-26159, 10 $\mu$g/inj., s.c., b.i.d., q.d. 1-18 | 712 ± 363 | 28 |

[1] Data reported as means ± s.e.m. on 8 animals in control and test groups.
[2] % Test/Control = Test tumor size/Control tumor size × 100

Five other bombesin analogs were also tested for their antitumor activity by the subcutaneous assay and the results are shown in Table 3. Three analogs, BIM-26189, BIM-26217, BIM-26217, reduced growth of the implanted hepatoma by 44%, 30% and 17%, respectively, over a period of 18 days. Two analogs, BIM-26223 and BIM-26228, on the other hand, slightly stimulated growth of the tumor cells.

TABLE 3

| Treatment | Tumor Weight (mg)[1] Day 18 | % Test/ Control |
| --- | --- | --- |
| Vehicle treated control, 0.2 ml/inj., s.c. | 578.7 ± 145.6 | — |
| BIM-26189, 100 μg/inj., s.c., b.i.d., q.d. 1-20 | 324.9 ± 79.0 | 56 |
| BIM-26187, 100 μg/inj., s.c., b.i.d., q.d. 1-20 | 482.8 ± 175.0 | 83 |
| BIM-26218, 100 μg/inj., s.c., b.i.d., q.d. 1-20 | 402.8 ± 147.1 | 70 |
| BIM-26223, 100 μg/inj., s.c., b.i.d., q.d. 1-20 | 722.9 ± 218.5 | 125 |
| BIM-26228, 100 μg/inj., s.c., b.i.d., q.d. 1-20 | 667.2 ± 181.6 | 115 |

[1]Tumor weight reported as means ± s.e.m. on 10 animals in control group and 6 in the test group.

Use

Bombesin analogs, as shown in formulae (A) and (B) can be used for the in vivo treatment of liver cancer.

The amount to be administered, will depend upon the condition being treated, the route of administration chosen, and the specific activity of the analog, and ultimately will be decided by the attending physician or veterinarian. Such amount of the active analog as determined by the attending physician or veterinarian is referred to herein as a "therapeutically effective amount" and is preferably in the range of 100 μg/kg/day to 50 mg/kg/day.

The analog may be administered by any route appropriate to the condition being treated. Preferably, the analog is injected into the bloodstream of the subject being treated. However, it will be readily appreciated by those skilled in the art that the route, such as intravenous, subcutaneous, intramuscular, intraperitoneal, nasal, oral, etc., will vary with the condition being treated and the activity of the analog being used.

While it is possible for the bombesin analog to be administered as the pure or substantially pure compound, it is preferable to present it as a pharmaceutical formulation or preparation.

The formulations of the present invention, both for veterinary and for human use, comprise a peptide analog of the invention, as above described, together with one or more pharmaceutically acceptable carriers therefor, and optionally other therapeutic ingredients.

The carrier must be "acceptable" in the sense of being compatible with the active ingredient(s) of the formulation (and preferably, capable of stabilizing peptides) and not deleterious to the subject to be treated. Desirably, the formulation should not include oxidizing agents or other substances with which peptides are known to be incompatible. For example, bombesin analogs in the cyclized form are oxidized; thus, the presence of reducing agents as excipients could lead to an opening of the cystine disulfur bridge. On the other hand, highly oxidative conditions can lead to the formation of cysteine sulfoxide and to the oxidation of Tryptophane. Consequently, it is important to carefully select the excipient. As pointed out previously, pH is another key factor and it is necessary to buffer the product under slightly acidic conditions (pH 5 to 6).

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary as in the case of tablets, forming the product into the desired shape and size.

Formulations suitable for intravenous administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Other Embodiments

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed is:

1. The method for treating hepatoma in a mammalian subject, which method includes administering to said subject a composition comprising a therapeutically effective amount of a bombesin analog of the formula:

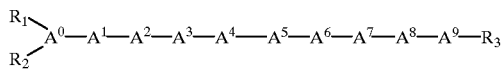

wherein
- $A^0$ is Gly, a D- or L-isomer selected from the group consisting of pGlu, Nle, α-aminobutyric acid, Ala, Val, Gln, Asn, Leu, Ile, p-X-Phe (where X is H, F, Cl, Br, $NO_2$, OH, or $CH_3$), Trp, β-Nal, and Cys, or is deleted;
- $A^1$ is a D- or L-isomer selected from the group consisting of pGlu, Nle, α-aminobutyric acid, Ala, Val, Gln, Asn, Leu, Ile, p-X-Phe (where X is He F, Cl, Br, $NO_2$, OH, or $CH_3$) Asp, Glu, $F_5$-Phe, Trp, β-Nal, Cys, and Lys, or deleted;
- $A^2$ is Gly, a D- or L-isomer selected from the group consisting of pGlu, Ala, Val, Gln, Asn, Leu, Ile, p-X-Phe (where X is Hs Fe Cl, Br, $NO_2$, OH, or $CH_3$) Trp, β-Nal, Asp, Glu, His, 1-methyl-His, 3-methyl-His, Cys, and Lys, or deleted;
- $A^3$ is a D- or L-isomer selected from the group consisting of p-X-Phe (where X is H, F, Cl, Br, $NO_2$, OH, or $CH_3$), β-Nal, and Trp;
- $A^4$ is Ala, Val, Gln, Asn, Gly, Leu, Ile, Nle, α-aminobutyric acid, p-X-phe (where X is H. F, Cl, Br, $NO_2$, OH, or $CH_3$), Trp, or β-Nal;
- $A^5$ is Gln, Asn, Gly, Ala, Leu, Ile, Nle, α-aminobutyric acid, Val, p-X-Phe (where X is He F, Cl, Br, $NO_2$, OH, or $CH^3$), Trp, Thr, or β-Nal;
- $A^6$ is Sar, Gly, a D-isomer selected from the group consisting of Ala, N-methyl-Ala, Val, Gln, Asn, Leu, Ile, p-X-Phe (where X is H, Fe Cl, Br, $NO_2$, OH, or $CH_3$), Trp, Cys, and β-Nal, or deleted;
- $A^7$ is 1-methyl-His, 3-methyl-His, His, Lys, Asp, or Glu;
- $A^8$ is Leu, Ile, Val, Nle, α-aminobutyric acid, Trp, Thr, β-Nal, Lys, Asp, Glu, or Cys;
- $A^9$ is L-isomer of any of Met, Met-oxide, Leu, Ile, Nle, α-aminobutyric acid, p-X-Phe (where X is H, F, Cl, Br, $NO_2$, OH, or $CH_3$), Trp, β-Nal, CHxAla, Cys, or deleted;

each $R_1$ and $R_2$, independently, is H, $C_{1-12}$ alkyl, $C_{7-10}$ phenylalkyl, $COE_1$ (where $E_1$ is $C_{1-20}$ alkyl, $C_{3-20}$ alkenyl, $C_{3-20}$ alkynyl, phenyl, naphthyl, or $C_{7-10}$ phenylalkyl), or $C_1$–$C_{12}$ acyl, and $R_1$ and $R_2$ are bonded to the nitrogen adjacent to the -carbon of the N-terminal amino acid residue of the analog; provided that when one of $R_1$ or $R_2$ is $COE_1$, the other must be H; and $R_3$ is OH, $NH_2$, $C_{1-12}$ alkoxy, $C_{7-10}$ phenylalkoxy, or $C_{3-20}$ naphthylalkoxy and is bonded to the -carbonyl carbon of the C-terminal amino acid residue of the analog;

provided that, if $A^0$ is present, $A^1$ cannot be pGlu; and, if $A^0$ or $A^1$ is present, $A^2$ cannot be pGlu; further provided that, when $A^0$ is deleted and $A^1$ is pGlu, one of $R^1$ and $R^2$ must be H; further provided that, where $A^0$ is deleted and $A^1$ is not pGlu, -amino group of $A^1$ can be coupled with -carboxyl group of $A^9$ through an amide bridge, or where $A^0$ and $A^1$ are deleted and $A^2$ is not PGlu, -amino group of $A^2$ can be coupled with -carboxyl group of $A^9$ through an amide bridge, or where $A^0$, $Al^1$, and $A^2$ are deleted, -amino group of $A^3$ can be coupled with -carboxyl group of $A^9$ through an amide bridge; further provided that both terminal residues cannot be Asp or Glu and Lys, respectively, and that side chain carboxyl group of Asp or Glu can be coupled with $\epsilon$-amino group of Lys through an amide bridge; further provided that either one of $A^1$ or $A^2$ can be Cys and coupled with one of $A^8$ or $A^9$ through a disulfide bridge, where one of $A^8$ or $A^9$ is cys; and further provided that where $A^0$ and $A^1$ are deleted and $A^6$ is D-Ala, $A^8$—$A^9$—$R_3$ cannot be Leu-Met-$NH_2$ or a pharmaceutically acceptable salt thereof.

2. The method of claim 1, wherein
$A^0$ is pGlu, Gly, D-Phe, or is deleted;
$A^1$ is pGlu, D-Phe, D-Ala, D-$\beta$-Nal, D-Cpa, D-Asn, Cys, or is deleted;
$A^2$ is pGlu, Asn, Gln, His, 1-methyl-His, 3-methyl-His, Cys, or is deleted;
$A^3$ is Trp;
$A^4$ is Ala;
$A^5$ is Val;
$A^6$ is Sar, Gly, D-Phe, or D-Ala;
$A^7$ is His;
$A^8$ is Leu or Cys;
$A^9$ is L-isomer of any of Met, Leu, Ile, Nle, Phe, or Cys.

3. The method of claim 2, wherein said analog is of the formula:
D-Phe-Gln-Trp-Ala-Val-Gly-His-Leu-Met-$NH_2$.

4. The method of claim 2, wherein said analog is of the formula:
D-Phe-Gln-Trp-Ala-Val-Gly-His-Leu-Leu-$NH_2$.

5. The method of claim 1, wherein said composition further comprises a pharmaceutically acceptable carrier.

6. The method of claim 1, wherein said composition is administered to said subject enterally, parenterally, transdermally, or transmucosally.

7. The method for treating hepatoma in A mammalian subject, which method includes administering to said subject a composition comprising a therapeutically effective amount of a bombesin analog of the formula:

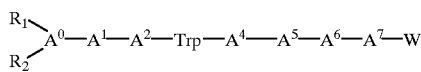

wherein
$A^0$ is pGlu, Gly, Nle, $\alpha$-aminobutyric acid, a D-isomer selected from the group consisting of Ala, Val, Gln, Asn, Leu, Ile, Net, p-X-Phe (where X is F, Cl, Br, $NO_2$, OH, H, or $CH_3$), Trp, Cys, and $\beta$-Nal, or deleted;
$A^1$ is a D- or L-isomer selected from the group consisting of pGlU, Nle, a-aminobutyric acid, a D-isomer selected from the group consisting of Ala, Val, Gln, Asn, Leu, Ile, Met, p-X-Phe (where X is F, Cl, Br, $NO_2$, OH, H, or $CH_3$), $F_5$-Phe, Trp, Cys, and $\beta$-Nal, or deleted;
$A^2$ is pGlu, Gly, Ala, Val, Gln, Asn, Leu, Ile, Met, p-X-Phe (where X is Ft Cl, Br, $NO_2$, OH, H, or $CH_3$), Trp, Cys, $\beta$-Nal, His, 1-methyl-His, or 3-methyl-His;
$A^4$ is Ala, Val, Gln, Asn, Gly, Leu, Ile, Nle, $\alpha$-aminobutyric acid, Met, p-X-Phe (where X is F, Cl, Br, $NO_2$, OH, H, or $CH_3$), Trp, Cys, or $\beta$-Nal;
$A^5$ is Gln, Asn, Gly, Ala, Leu, Ile, Nle, $\alpha$-aminobutyric acid, Met, Val, p-X-Phe (where X is F, Cl, Br, OH, H, or $CH_3$), Trp, Thr, or $\beta$-Nal;
$A^6$ is Sar, Gly, a D-isomer selected from the group consisting of Ala, N-methyl-Ala, Val, Gln, Asn, Leu, Ile, Met, p-X-Phe (where X is Fe Cl, Br, $NO_2$, OH, H, or $CH_3$), Trp, Cys, and $\beta$-Nal;
$A^7$ is 1-methyl-His, 3-methyl-His, or His;
each $R_1$ and $R_2$, independently, is H, $C_{1-12}$ alkyl, $C_{7-10}$ phenylalkyl, $COE_1$ (where $E_{,1}$ is $C_{1-20}$ alkyl, $C_{3-20}$ alkenyl, $C_{3-20}$ alkynyl, phenyl, naphthyl, or $C_{7-10}$ phenylalkyl), or $C_1$–$C_{12}$ acyl, provided that when one of $R_1$ or $R_2$ is $COE_1$, the other must be H; and each $R_1$ and $R_2$, independently, is bonded to the nitrogen adjacent to the -carbon of the N-terminal amino acid residue of the analog;
W is bonded to the -carbonyl carbon of $A^7$ and is one of the following groups: (I):

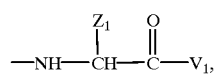

wherein $R_3$ is $CHR_{20}$—$(CH_2)_{n1}$ (where $R_{20}$ is either of H or OH; and n1 is either of 1 or 0), or is deleted, and $Z_1$ is the identifying group of an amino acid selected from the group consisting of Gly, Ala, Val, Leu, Ile, Ser, Asp, Asn, Glu, Gln, p-X-Phe (where X is H, P, Cl, Br, $NO_2$, OH, or $CH_3$) $F_5$-Phe, Trp, Cys, Met, Pro, HyPro, cyclohexyl-Ala, and $\beta$-Nal; and $V_1$ is either $Or_4$, or

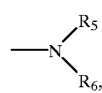

where $R_4$ is $C_{1-20}$ alkyl, $C_{3-20}$ alkenyl, $C_{3-20}$ alkynyl, phenyl, naphthyl, or $C_{7-10}$ phenylalkyl, and each $R_5$, and $R_6$, independently, is H, $C_{1-12}$ alkyl, $C_{7-10}$ phenylalkyl, lower acyl, or,

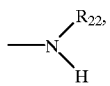

where $R_{22}$ is H, $C_{1-12}$ alkyl, $C_{7-10}$ phenylalkyl, or lower acyl; provided that, when one of $R_5$ or $R_6$ is —$NHR_{22}$, the other is H;

(II):

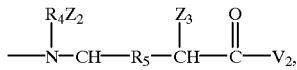

wherein $R_5$ is $CH_2$—NH, $CH_2$—S, $CH_2$—O, CO—$CH_2$, $CH_2$—CO, or $CH_2$—$CH_2$, and each $Z_2$ and $Z_3$, independently, is the identifying group of an amino acid selected from the group consisting of Gly, Ala, Val, Leu, Ile, Ser, Asp, Asn, Glu, Gln, β-Nal, p-X-Phe (where X is H, F, Cl, Br, $NO_2$, OH, or $CH_3$), $F_5$-Phe, Trp, Cys, Met, Pro, HyPro, and cylcohexyl-Ala; and $V_2$ is either $OR_6$ or

where each $R_4$, $R_6$, $R_7$, and $R_8$, independently, is H, lower alkyl, lower phenylalkyl, or lower naphthylalkyl;

(III):

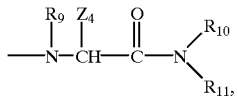

wherein $Z_4$ is the identifying group of an amino acid selected from the group consisting of Gly, Ala, Val, Leu, Ile, Ser, Asp, Asn, Glu, p-Nal, Gln, p-X-Phe (where X is H, Ft Cl, Br, $NO_2$, OH, or $CH_3$), $F_5$-Phe, Trp, Cys, Met, Pro, and HyPro; and each $R_9$, $R_{10}$, and $R_{11}$, independently, is H, lower alkyl, lower phenylalkyl, or lower naphthylalkyl; or (IV):

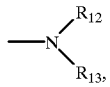

wherein each $R_{12}$ and $R_{13}$, independently, is H, lower alkyl, lower phenylalkyl, lower naphthylalkyl;

provided that, if $A^0$ is present, $A^1$ cannot be pGlu; further provided that, if $A^0$ or $A^1$ is present, $A^2$ cannot be pGlu; further provided that, when $A^0$ is deleted and $A^1$ is pGlu, one of $R_1$ and $R_2$ must be H; further provided that when either of $R_{12}$ or $R_{13}$ is other than H, $A^7$ is His, $A^6$ is Gly, $A^5$ is Val, $A^4$ is Ala, $A^2$ is His, and when either of $R_1$ or $R_2$ is other than H, $A^1$ must be other than deleted; further provided that $A^1$ can be coupled with $Z_3$ through a disulfide bridge, where $A^1$ is Cys and $Z_3$ is the identifying group of Cys; and further provided that, for the groups (I) through (IV), any asymmetric carbon atom can be R, S or a racemic mixture; or a pharmaceutically acceptable salt thereof.

8. The method of claim 7, wherein $A^0$ is Gly, D-Phe, or is deleted;

$A^1$ is p-Glu, D-Phe, D-Ala, D-P-Nal, D-Cpa, or D-Asn;

$A^2$ is Gln, His, 1-methyl-His, or 3-methyl-His;

$A^4$ is Ala;

$A^5$ is Val;

$A^6$ is Sar, Gly, D-Phe, or D-Ala;

$A^7$ is His; and, where W is (I) and $R_3$ is $CH_2$ or $CH_2$—$CH_2$, $Z_1$ is the identifying group of Leu or Phe; where W is (I) and $R_3$ is CHOH—$CH_2$, $Z_1$ is the identifying group of Leu, CHxAla, or Phe and each $R_5$ and $R_6$ is H; and where W is (I), $V_1$ is $NHR_6$ and $R_6$ is $NH_2$; where W is (II) and $R_5$ is $CH_2$—NH, each $Z_2$ and $_3$, independently, is the identifying group of Leu or Phe; where W is (III), $Z_4$ is the identifying group of any one of Leu or p-X-Phe (where X is H, F, Cl, Br, $NO_2$, OH, or $CH_3$); and each $R_9$, $R_{10}$ and $R_{11}$, independently, is H, lower alkyl, lower phenylalkyl, or lower naphthylalkyl; and where W is (IV), each $R_{12}$ and $R_{13}$ is H and each $R_1$ and $R_2$, independently, is H, lower alkyl, or lower acyl.

9. The method of claim 8, wherein said analog is of the formula:

D-Cpa-Gln-Trp-Ala-Val-Gly-His-Leu-ψ[$CH_2$ NH]-Phe-$NH_2$.

10. The method of claim 8, wherein said analog is of the formula:

D-Phe-Gln-Trp-Ala-Val-Gly-His-Leu-ψ[$CH_2$ NH]-Cpa-$NH_2$.

11. The method of claim 7, wherein $A^0$ is deleted, $A^2$ is Gln, and W is (I) with $R_3$ being deleted and $V_1$ being $OR_4$ where $R_4$ is any of $C_{1-20}$ alkyl, C3-20 alkenyl, $C_{3-20}$ alkynyl, phenyl, naphthyl, or $C_{7-10}$ phenylalkyl.

12. The method of claim 11, wherein said analog is of the formula:

D-Phe-Gln-Trp-Ala-Val-N-methyl-D-Ala-His-Leu-methylester.

13. The method of claim 11, wherein said analog is of the formula:

D-$F_5$-Phe-Gln-Trp-Ala-Val-D-Ala-His-Leu-methylester.

14. The method of claim 7, wherein said composition further comprises a pharmaceutically acceptable carrier.

15. The method of claim 7, wherein said composition is administered to said subject enterally, parenterally, transdermally, or transmucosally.

* * * * *